United States Patent
Miller et al.

(10) Patent No.: US 7,838,256 B2
(45) Date of Patent: Nov. 23, 2010

(54) ASSAY AND KIT FOR DRUG EFFLUX TRANSPORTER ACTIVITY

(75) Inventors: Donald W. Miller, Winnepeg (CA); Corbin J. Bachmeier, Minot, ND (US); Richard B. Lomneth, Omaha, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 612 days.

(21) Appl. No.: 11/678,209

(22) Filed: Feb. 23, 2007

(65) Prior Publication Data

US 2008/0206781 A1 Aug. 28, 2008

(51) Int. Cl.
*G01N 33/53* (2006.01)
*C40B 30/04* (2006.01)

(52) U.S. Cl. .................. 435/7.21; 435/7.2; 435/7.1; 435/6; 435/4

(58) Field of Classification Search ............... 435/7.21, 435/7.2, 7.1, 6, 4
See application file for complete search history.

(56) References Cited

U.S. PATENT DOCUMENTS

| 5,766,875 A * | 6/1998 | Hafeman et al. ............... 435/29 |
| 6,277,655 B1 | 8/2001 | Sarkadi et al. |
| 6,391,656 B2 | 5/2002 | Sarkadi et al. |
| 2003/0044316 A1 * | 3/2003 | Hirai et al. ..................... 422/56 |
| 2005/0130236 A1 * | 6/2005 | Goldman .................... 435/7.21 |

FOREIGN PATENT DOCUMENTS

WO 96/06945 3/1996

OTHER PUBLICATIONS

Homolya, L., et. al., "Fluorescent cellular indicators are extruded by the multidrug resistance protein," J. Biol. Chem., 268(29):21493-96, (Oct. 15, 1993).
Hollo, Z., et al., "Calcein accumulation as a fluorometric functional assay of the multidrug transporter," Biochim. Biophys. Acta., 1191(2):384-8, (1994).
Zhang, Y., et al., "In vitro and in vivo models for assessing drug efflux transporter activity," Adv. Drug Del. Rev., 55:31-51, (2003).
Brezden, C.B., et al., "Constitutive expression of P-glycoprotein as a determinant of loading with fluorescent calcium probes," Cytometry, 17:343-348, (1994).
Feller, N., et al., "ATP-dependent efflux of calcein by the multidrug resistance protein (MRP): no inhibition by intracellular glutathione depletion," FEBS Lett., 368:385-388 (1995).
Goodfellow, H.R., et al., "Protein kinase C-mediated phosphorylation does not regulate drug transport by the human multidrug resistance P-glycoprotein," J. Biol. Chem., 271(23):13668-74, (Jun. 7, 1996).
Hollo, Z., et al., "Transport properties of the multidrug resistance-associated protein (MRP) in human tumour cells," FEBS Lett., 383:99-104, (1996).
Essodaigui, M., et al., "Kinetic analysis of calcein and calcein—acetoxymethylester efflux mediated by the multidrug resistance protein and P-glycoprotein," Biochemistry, 37(8):2243-50, (1998).
Tang-Wai, D.F., et al., "Human (MDR1) and mouse (mdr1,mdr3) P-glycoproteins can be distinguished by their respective drug resistance profiles and sensitivity to modulators," Biochemistry, 34(1):32-39, (1995).
Millot, J-M., et al., "Scanning microspectrofluorometry of rhodamine 123 in multidrug-resistant cells," Cytometry, 17:50-58, (1994).
Nare, B., et al., "Characterization of rhodamine 123 binding to P-glycoprotein in human multidrug-resistant cells," Mol. Pharmacol., 45:1145-52, (1994).
Altenberg, G.A., et al., "Unidirectional fluxes of rhodamine 123 in multidrug-resistant cells: evidence against direct drug extrusion from the plasma membrane," Proc. Natl. Acad. Sci. USA, 91:4654-4657, (May 1994).
Van Amersfoort, E.S., et al.,"Evaluation of a flow cytometric fluorescence quenching assay of phagocytosis of sensitized sheep erythrocytes by polymorphonuclear leukocytes," Cytometry, 17(4):294-301, (1994).
Beyersman, D., et al., "The genetic toxicology of cobalt," Toxicol. Appl. Pharmacol., 115(1):137-45, (1992).
Bachmeier, C.J., et al., "A fluorometric screening assay for drug efflux transporter activity in the blood-brain barrier," Pharmaceutical Research, 22(1):115-121, (Jan. 2005).

* cited by examiner

*Primary Examiner*—Teresa D. Wessendorf
(74) *Attorney, Agent, or Firm*—Patrick J. Hagan; Dann, Dorfman, Herrell and Skillman, P.C.

(57) ABSTRACT

The present invention relates to high-throughput cell-based assays for real-time monitoring of multi-resistant drug protein activity. The present invention is an improvement over existing assays in that in addition to a fluorescent drug efflux probe as an indicator of MDR protein activity, the instant assays provide an o-tolidine-based dye for quenching extracellular fluorescence of the probe.

4 Claims, 3 Drawing Sheets

ASSAY AND KIT FOR DRUG EFFLUX TRANSPORTER ACTIVITY

INTRODUCTION

This invention was made with government support under Grant No. R01-CA93558 awarded by the National Institutes of Health. The government has certain rights in the invention.

BACKGROUND OF THE INVENTION

The efficiency of chemotherapeutic treatment of tumors is hindered by the onset of multi-drug resistance (MDR) resulting from the overexpression of certain membrane-bound proteins in cancer cells. These membrane-bound MDR proteins include the MDR1 protein (alternatively termed P-glycoprotein), MRPs, and their functional analogs, breast cancer resistance protein (BCRP) and others. Cytostatic agents, e.g., Vinca alkaloids, anthracycline derivatives and other clinically effective anti-cancer agents are actively transported out of cancer cells by these MDR proteins, thereby decreasing their efficacy.

These same transport proteins are expressed in normal cells including the epithelial cells of the intestine, liver, kidney and placenta, and brain endothelial cells that form the blood-brain barrier (BBB). The presence of MDR transport proteins in these normal cells can have adverse effects on the absorption, distribution and elimination properties of many drugs and xenobiotics.

Cell permeable, hydrophobic ester derivatives of some fluorescent dyes are also actively exported from cells by MDR proteins. However, when the ester derivatives reach the cytosol, intracellular esterases cleave the esters in the fluorescent dyes, and the MDR1 proteins fail to export the resulting free dye compounds (Homolya, et al. (1993) *J. Biol. Chem.* 268:21493-96). It has been demonstrated that the commercially available compound, calcein-AM (calcein-acetoxy-methylester) is, unlike free calcein, an activator of the MDR-dependent ATPase. It has also been shown that calcein accumulation in the cell following calcein-AM uptake is reduced by the presence of MDR1 activity. Likewise, other MDR proteins such as the MRPs export free calcein from cells. This activity of MRP proteins decreases cellular levels of calcein, thereby decreasing fluorescence. Thus, expression of either MDR1 or MRPs leads to decreased cellular fluorescence.

It has been demonstrated that calcein-AM is useful for the functional analysis of the presence of multi-drug resistance in cells (Hollo, et al. (1994) *Biochim. Biophys. Acta.* 1191(2): 384-8; U.S. Pat. Nos. 6,391,656 and 6,277,655; WO 96/06945). Cells overexpressing MDR proteins export the penetrating calcein-AM molecules via an active transport mechanism, and thus the rate of transformation of calcein-AM to fluorescent calcein (or other fluorescent calcein derivatives) and the rate of accumulation of the fluorescent product(s) within the cells are significantly reduced relative to wild-type cells.

Commercially available fluorescent dye-based kits such the MULTIDRUG RESISTANCE DIRECT DYE EFFLUX ASSAY™ available from Chemicon International, Inc. (Temecula, Calif.), the MULTIDRUGQUANT™ Assay Kit available from Solvo Biotechnology (Budapest, Hungary) and the VYBRANT™ Multidrug Resistance Assay Kit available from INVITROGEN™-MOLECULAR PROBES™ (Carlsbad, Calif.) can be used for detecting MDR protein activity, however, these assays generally require washing steps to remove extracellular solutions. Therefore, these assays are time consuming and generally do not provide real-time MDR protein activity, thus providing limited data.

Drug resistance profiling is also of interest in the clinical setting to determine substrate specificity and drug efflux activity of the various multi-drug resistance proteins in a given tumor sample. Therefore, there is a need in the art for a rapid, highly sensitive, reproducible in vitro multi-drug resistance assay to demonstrate transport activity of various multi-drug resistance proteins (e.g., MDR1, MRP1, cMOAT) in the plasma membrane. The present invention meets this need in the art.

SUMMARY OF THE INVENTION

The present invention is a high-throughput method for real-time monitoring of multi-drug resistance (MDR) protein activity of a cell. Monitoring of MDR protein activity involves the steps of contacting a cell expressing a multi-drug resistance protein with a fluorescent drug efflux probe and an o-tolidine-based dye for quenching the extracellular fluorescence of the probe; and determining the intracellular accumulation of the fluorescent drug efflux probe in the cell.

The present invention is also a real-time, high-throughput method for identifying a modulator of a multi-drug resistance protein. Identification of modulators of a MDR protein involves the steps of contacting a cell expressing a multi-drug resistance protein with a test agent, a fluorescent drug efflux probe, and an o-tolidine-based dye for quenching the extracellular fluorescence of the probe; and determining the intracellular accumulation of the fluorescent drug efflux probe in the cell, wherein an increase in the intracellular accumulation of the fluorescent drug efflux probe is indicative of a multi-drug resistance protein inhibitor and a decrease in the intracellular accumulation of the fluorescent drug efflux probe is indicative of a multi-drug resistance protein activator.

The present invention is further a real-time, high-throughput method for diagnosing drug resistance of a cell to therapeutic agents. This method involves the steps of contacting a cell suspected of overexpressing a multi-drug resistance protein with a fluorescent drug efflux probe and an o-tolidine-based dye for quenching the extracellular fluorescence of the probe; and determining the intracellular accumulation of the fluorescent drug efflux probe in the cell, wherein a decrease in the accumulation of the fluorescent drug efflux probe in the cell as compared to a control or standard is indicative of drug resistance of the cell to therapeutic agents.

A kit for real-time, high-throughput monitoring of multi-drug resistance protein activity is also provided, said kit comprising a fluorescent drug efflux probe and an o-tolidine-based dye for quenching the extracellular fluorescence of the probe.

BRIEF DESCRIPTION OF THE DRAWINGS

FIG. 1A); human, Caucasian, colon adenocarcinoma cells (Caco2; FIG. 1B); and bovine brain microvessel endothelial cells (BBMEC, FIG. 1C) exposed to MDR1 inhibitor GF120918, MRP inhibitor indomethacin, or GF120918 in combination with indomethacin. Trypan blue (0.04%) was used to quench extracellular fluorescence.

DETAILED DESCRIPTION OF THE INVENTION

Figure 1A:
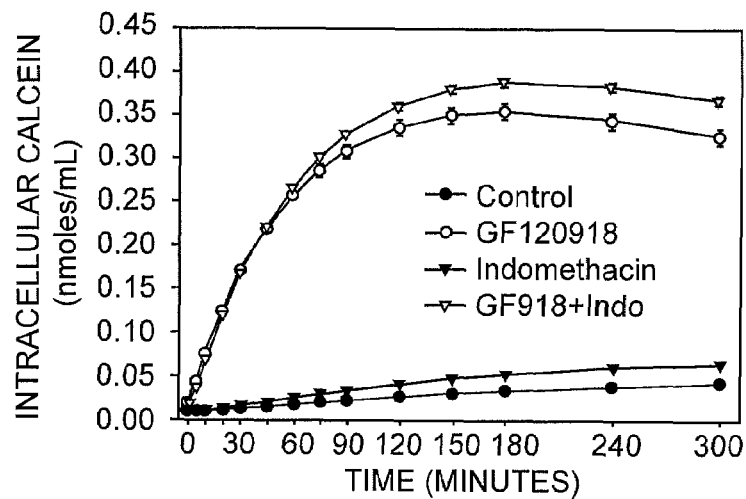
FIGS. 1A-1C show intracellular accumulation of calcein-AM (1 µM) in Madin-Darby canine kidney cells transfected with human MDR1 gene (MDCK-MDR1.

Because MDR1 and MRP influence drug absorption and distribution and elimination of a wide variety of drugs, the identification of potential drug efflux transporter interactions is of fundamental importance in drug discovery and development. It has now been found that the speed and sensitivity of cell-based assays using fluorescent probes as indicators of MDR protein activity can be increased by quenching extracellular fluorescence of the probes. Specifically, it has been found that contacting a cell with a fluorescent drug efflux probe in the presence of an o-tolidine-based dye improves the detection of intracellular accumulation of the probe. Because the instant cell-based assays do not require laborious washing steps for detecting intracellular fluorescence, high-throughput screening and real-time monitoring of MDR protein activity is now possible. Moreover, because similar drug efflux transporters are present in drug-resistant bacteria and parasites, the instant assay can be adapted to screening for antibiotics and antihelmetics.

The real-time assays disclosed herein offer the advantage of allowing cellular events (i.e., intracellular accumulation of a fluorescent drug efflux probe) to be monitored at the actual time during which the events take place. This is in contrast to prior art assays in which the accumulation of fluorescent probe within a cell is detected after cells have been washed to remove assay reagents or detected by flow cytometry.

Assays disclosed herein are high-throughput in the sense that these assays are carried out in a 96-well or higher density format (e.g., 384- or 1536-well plates). Desirably, such assays demonstrate a signal of sufficient intensity that it can be easily measured from a microtiter plate in low volume and have a suitable signal-to-background ratio and coefficient of variation determined from measurements across the entire plate (these factors are typically expressed as the statistical parameter, Z', which has an acceptable lower limit of 0.5). Advantageously, high-throughput assays of the instant invention are labor efficient as they can be used in combination with well-known robotic systems. Accordingly, cells used in accordance with the instant assay can be configured in a biochip format for monitoring, screening and diagnostic assays.

The high-throughput real-time assays of the present invention are useful for detecting the activity of a variety of multi-drug resistance (MDR) proteins. Generally, MDR proteins are membrane-bound proteins that can transport a given compound through the cell membrane even against the concentration gradient by using the energy obtained through ATP hydrolysis. MDR1 or P-glycoprotein (Pgp) is a membrane-bound protein of 170 kD, functional expression of which causes multi-drug resistance of a given cell. MRP or Multi-drug Resistance Protein is a 190 kDa glycoprotein belonging to a family of efflux pumps, functional expression of which confers multi-drug resistance on a given cell by mediating the ATP-dependent membrane transport of glutathione S-conjugates of chemotherapeutic drugs. In the context of the present invention the gene products of the MDR1 gene (ABCB1), MRP gene (ABCC1), and functional analogs thereof are collectively referred to herein as MDR proteins without regard to their source or to common names. In other words, the term "MDR protein" encompasses proteins causing multi-drug resistance of a cell including both eukaryotic and prokaryotic cells, i.e., cells from mammals and parasites as well as bacterial cells.

Functional analogs of a protein are also generally structural homologues of the protein. For example, a membrane transport protein that can export compounds from a cell which are detrimental to a function of the cell through an active transport mechanism are embraced herein as functional analogs of the MDR1 or MRP protein.

Multi-drug resistance denotes the occurrence of MDR protein-mediated efflux (i.e., active transport) of a compound in a cell or cells. While such cellular efflux facilitates transport of a variety of substances to the outside of the cell membrane, such transport is particularly problematic in tumor cells, wherein it typically interferes with therapeutic treatment of cancer due to the active transport of a wide variety cytotoxic and cytostatic agents of significantly different structure to the exterior of the cell membrane. Such tumor cells generally overexpress MDR proteins when compared to expression of MDR proteins in normal cells. By virtue of overexpression of MDR proteins, these cells are generally referred to as "multi-drug resistant" or "drug resistant" cells. As will be appreciated by the skilled artisan, "multi-drug resistant" or "drug resistant" cells encompasses not only drug resistant tumor cells, but also drug resistant bacteria and drug resistant parasites. Because these same drug efflux proteins are expressed in the intestinal epithelial cells that provide a cellular barrier between ingested material and the bloodstream, and the endothelial cells that form the blood-brain barrier, drug resistant epithelial cells can also contribute to poor oral absorption and limited tissue distribution of a drug. Thus, the terms "multi-drug resistant" or "drug resistant" cells can also apply to epithelial cells of the intestine and blood-brain barrier. See, Zhang, et al. (2003) *Adv. Drug Del. Rev.* 55:31-51 for examples of drug resistant cells and in vitro drug efflux transporter screening assays using the same.

As is well-known in the art, activity of MDR proteins is detectable by the active transport of probes which, like therapeutic agents, are substrates for MDR proteins. In this regard, the instant assays employ a fluorescent drug efflux probe, also referred to herein simply as a probe, to detect and monitor the activity of MDR proteins. As used in the context of the present invention, a "fluorescent drug efflux probe" is a compound, the presence and/or concentration of which, can be accurately determined by the naked eye or by instrumental measurement based on fluorescence of the compound. These compounds are said to be "drug efflux probes" as their export from the cell is indicative of the export of a therapeutic agent or drug from the cell by MDR proteins expressed by the cell.

Acetoxymethyl (AM) ester derivatives of fluorescent calcium indicators such as indo-1-AM and fluo-3-AM or other dyes such as BCECF-AM and calcein-AM, are rapidly exported from cells expressing MDR1 (Brezden, et al. (1994) *Cytometry* 17:343-348). As such, this class of highly sensitive probes is suitable for use in the functional assays of the instant invention. Calcein-AM, but not calcein, is an activator of MDR1 in isolated membranes with a $K_d \leq 1$ µM (Homolya, et al. (1993) supra). Cells expressing MDR1 rapidly remove the non-fluorescent probe calcein-AM, resulting in decreased accumulation of the highly fluorescent calcein in the cytoplasmic compartment (Feller, et al. (1995) *FEBS Lett.* 368: 385-388; Homolya, et al. (1993) supra; Goodfellow, et al. (1996) *J. Biol. Chem.* 271:13668-74). Calcein-AM is also a substrate for the MDR-associated protein (MRP), although in this case it is the hydrophilic free calcein anion that is exported (Hollό, et al. (1996) *FEBS Lett.* 383:99-104; Essodaigui, et al. (1998) *Biochemistry* 37:2243-50). Because calcein itself is not a substrate for MDR1, MDR protein activity can be quantitatively assessed by measuring the net accumulation of intracellular fluorescence. The absorption and emission maxima of calcein (i.e., 494 and 517 nm, respectively) are ideally suited for detection by instruments such as conventional fluorimeters or scanning laser microscopes equipped with standard fluorescein filters.

MDR cells overexpressing the MDR1 have also been identified using various mitochondrial probes, including rhodamine 123, acridine orange 10-nonyl bromide, and rhodamine 6G (Tang-Wai, et al. (1995) *Biochemistry* 34:32-39; Millot, et al. (1994) *Cytometry* 17:50-58; Altenberg, et al. (1994) *J. Biol. Chem.* 269:7145-7149; Nare, et al. (1994) *Mol. Pharmacol.* 45:1145-52; Altenberg, et al. (1994) *Proc. Natl. Acad. Sci. USA* 91:4654-57). As exemplified herein, such fluorescent drug efflux probes are also suitable for use in accordance with the instant methods.

To decrease background fluorescence resulting from the presence of extracellular probe, the instant methods provide an o-tolidine-based dye such as trypan blue or Evans blue to quench the extracellular fluorescence of the fluorescent drug efflux probe. In one embodiment, the o-tolidine-based dye is trypan blue. O-tolidine-based dyes, also generally referred to herein as dyes, are dyes wherein the reduction product is o-tolidine. Such dyes do not readily diffuse across the plasma membrane of living cells but mask or quench the extracellular fluorescence of fluorescent drug efflux probe thereby facilitating the detection of intracellularly-localized probe. Accordingly, in particular embodiments, the instant assays are carried out without removing the extracellular solution or reagents.

It is contemplated that near-infrared fluorescent probes can also be used in accordance with the instant assays. Such probes include, but are not limited to, CY3, and CY5 and Rhodamine 800, which are structurally similar to substrates for drug efflux transport systems. Exemplary dyes for quenching the near-infrared fluorescent probes include the BLACK HOLE QUENCHER® Dyes (Biosearch Technologies, Inc., Novato, Calif.).

When assaying bacterial cells expressing a multi-drug resistance protein, it is envisioned that ethidium bromide can be used as the fluorescent drug efflux probe and Sudan Black dye or a BLACK HOLE QUENCHER® dye as the dye for quenching the extracellular fluorescence of the probe.

High-throughput real-time monitoring of MDR protein activity of a cell in accordance with the instant invention is carried out by simultaneously or consecutively contacting a cell expressing or overexpressing an MDR protein with a fluorescent drug efflux probe and an o-tolidine-based dye and determining the intracellular accumulation of the fluorescent drug efflux probe. A cell in accordance with the present invention includes, e.g., a blood-brain barrier endothelial cell, a drug-resistant cancer cell, a drug-resistant bacterial cell, a fungal cell, a plant cell and the like. In general, drug-resistant cells express elevated levels of MDR proteins compared to normal cells and therefore intracellular accumulation of the fluorescent drug efflux probe is less than that of a normal cell. The levels of intracellular accumulation of probe can be qualitatively or quantitatively determined depending upon the application of the instant method. In this regard, qualitative determinations can be carried out by detecting the relative presence or absence of fluorescence in the cell as compared to a control cell, e.g., a cell known to exhibit a high or low level of MDR protein activity. Conversely, quantitative determinations can be made using, e.g., a fluorimeter to measure an absolute amount of intracellular fluorescence. The absolute amount can be compared to an absolute amount of fluorescence in a control cell or to a standard (e.g., a known amount of fluorescence which correlates with a known concentration of probe).

Given the ability to monitor real-time intracellular accumulation of probe in cells expressing MDR proteins, this method of the invention finds application in continuous monitoring for changes in MDR protein activity over time. For example, a drug-resistant cell expressing an MDR protein is contacted with a probe and dye according to the invention and subsequently contacted with an inhibitor of MDR protein activity. Using real-time monitoring, quantitative kinetic analysis of MDR protein activity is performed to assess the effectiveness of the inhibitor (e.g., rate of accumulation of probe). In so far as protein expression modulates protein activity, the instant assay also finds application in the monitoring of repressors of gene expression. Likewise, quantitative evaluation of activators of MDR protein activity or inducers of drug efflux transporter protein expression, i.e., an agent that causes the cell to produce more transporter protein, is also possible. Therefore, when monitoring the activity of an MDR protein in accordance with the present invention, it should be understood that MDR protein activity also encompasses changes in MDR protein expression.

In this regard, the present invention is also a high-throughput real-time method for identifying an agent that modulates the activity or expression of a multi-drug resistance protein. As used in the context of the present invention, an agent that modulates the activity or expression of a MDR protein includes agents that inhibit, as well as agents that stimulate or activate, MDR protein activity or expression. Generally, an agent that stimulates the activity of an MDR protein is a compound that increases the amount or rate of export of a compound of interest (e.g., calcein-AM or a toxin). An inhibitor of a MDR protein is an agent that can block the active transport of a compound of interest (e.g., calcein-AM or a therapeutic drug) to the outside of the cell membrane. An inhibitor can be a general inhibitor or a selective inhibitor. A general inhibitor of an MDR protein serves to block substantially all active transport to the outside of the cell membrane, regardless of the type of transport protein that is being expressed in the cell. In contrast, a selective inhibitor serves to block only that transport that is due to a selected transport protein or pathway thereof. For example, verapamil blocks both MDR1- and MRP1-mediated cell efflux, and is a general inhibitor. In contrast, MK 571 blocks only MRP-mediated cell efflux, and is a selective inhibitor.

Modulators are identified by simultaneously or consecutively contacting a cell expressing a multi-drug resistance protein with a test agent, a fluorescent drug efflux probe and an o-tolidine-based dye for quenching the extracellular fluorescence of the probe; and determining the intracellular accumulation of the fluorescent drug efflux probe in the cell in response to the modulator. In particular embodiments, the cell being contacted is a tumor cell which exhibits a multi-drug resistance phenotype. The cell could also be a normal epithelial or endothelial cell which expresses the MDR phenotype. As disclosed herein, intracellular accumulation can be determined quantitatively or qualitatively using standard methods for detecting fluorescent compounds. Further, a determination of the intracellular accumulation of the fluorescent drug efflux probe in the cell can include a comparison with a control cell or a standard as described herein. Alternatively, intracellular accumulation can be determined based on a change in intracellular levels of the probe before (i.e., baseline) and after contacting the cell with the test agent or based on a comparison with a cell which has not been contacted with the test agent. Generally, a test agent which inhibits the activity or expression of an MDR protein will result in a decrease in the amount or rate of export of the probe and a concurrent increase in the intracellular accumulation of the probe. Conversely, a test agent which stimulates the activity or expression of an MDR protein will result in an increase in the amount or rate of export of the probe and a concurrent decrease in the intracellular accumulation of the probe.

Test agents which can be screened in accordance with the screening assay disclosed herein encompass numerous chemical classes, though typically they are organic molecules, preferably small organic compounds having a molecular weight of more than 100 and less than about 2,500 daltons. Libraries of compounds can contain either collections of pure agents or collections of agent mixtures. Examples of pure agents include, but are not limited to, proteins, antibodies, peptides, peptide aptamers, nucleic acids, oligonucleotides, carbohydrates, lipids, synthetic or semi-synthetic chemicals, and purified natural products. Such libraries are commercially available to the skilled artisan. Examples of agent mixtures include, but are not limited to, extracts of prokaryotic or eukaryotic cells and tissues, as well as fermentation broths and cell or tissue culture supernates. Moreover, inhibitory agents can be rationally designed from known inhibitors of MDR proteins such as MK 571; CCCP; GF120918; cyclosporin A; 2,4-DNP; probenecid; sulfinpyrazone; benzbromarone; indomethacin; N-ethylmaleimide; or prostaglandin A1.

Therapeutic agents found to interact with MDR proteins tend to have a limited oral bioavailability and/or a diminished distribution to certain tissues (e.g., brain). Therefore, early identification of therapeutic agents which are substrates for MDR proteins is an important step in the drug development process. Advantageously, monitoring and screening methods of the invention can be used to determine whether a therapeutic agent (e.g., an anticancer drug or antibiotic) is an activator of MDR proteins thereby decreasing the effectiveness of the therapeutic agent.

Inhibitors identified by the method disclosed herein are useful for increasing the efficacy of therapeutic agents known to be susceptible to drug-resistance phenotypes. Similarly, it is contemplated that MDR protein activators can be used in emergency situations wherein a subject has been exposed to a toxin and cellular export is desired. Accordingly, modulators of the invention can be formulated with appropriate carriers or diluents, which further can be pharmaceutically acceptable. The means of making such a pharmaceutical composition have been described in the art (see, for instance, Remington: The Science and Practice of Pharmacy, Alfonso R. Gennaro, editor, 20th ed. Lippincott Williams & Wilkins: Philadelphia, Pa., 2000). Certain pharmaceutical compositions are single unit dosage forms suitable for oral, mucosal (e.g., nasal, sublingual, vaginal, buccal, or rectal), parenteral (e.g., subcutaneous, intravenous, bolus injection, intramuscular, or intraarterial), or transdermal administration to a patient. Examples of dosage forms include, but are not limited to, tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The formulation should suit the mode of administration. For example, oral administration requires enteric coatings to protect the modulators of the invention from degradation within the gastrointestinal tract. In another example, the agents of the invention can be administered in a liposomal formulation to shield the modulators from degradative enzymes and facilitate transport in circulatory system.

The composition, shape, and type of dosage forms of the invention will typically vary depending on their use. For example, parenteral dosage form may contain smaller amounts of one or more of the active ingredients it contains than an oral dosage form used to treat the same disease. These and other ways in which specific dosage forms encompassed by the invention will vary from one another and are readily apparent to those skilled in the art.

To assess MDR protein activity in a clinical setting, the present invention is also a method for diagnosing drug resistance of a cell to therapeutic agents. In accordance with this method the cell being assayed is a cell suspected of overexpressing a multi-drug resistance protein (e.g., a cancer cell of a biopsy sample or prokaryotic cell isolated from a patient or environmental sample). Diagnosis of multi-drug resistance involves the steps of contacting a cell with a fluorescent drug efflux probe and an o-tolidine-based dye for quenching the extracellular fluorescence of said probe, and determining the intracellular accumulation of the fluorescent drug efflux probe in the cell. As with the other methods of the invention, intracellular accumulation can be quantitative or qualitative using standard methods for detecting fluorescent compounds. A cell exhibiting a decrease in the accumulation of the fluorescent drug efflux probe as compared to a control or standard (e.g., a normal control cell or fluorescent standard, respectively) is indicative of the cell being resistant to one or more therapeutic agents. Because a variety of MDR proteins are known, particular embodiments of this method embrace the use of general and selective inhibitors to determine which MDR protein is being overexpressed in the cell. For example, verapamil can be used to identify activity of MDR1 and MRP1, whereas MK 571 can be used to identify MRP-specific activity. Identifying the specific MDR protein being overexpressed in the cell provides the skilled clinician with a more rationale basis for choosing a therapeutic treatment regime which is not susceptible to a multi-drug resistance phenotype.

A kit for real-time, high-throughput monitoring of drug efflux transport protein activity is also provided herein. A kit of the invention comprises a fluorescent drug efflux probe and an o-tolidine-based dye for quenching the extracellular fluorescence of said probe. The kit may further include instructions for using the reagents, controls, standards, inhibitors, activators, microtiter plates, tubes, and the like.

The invention is described in greater detail by the following non-limiting examples.

Example 1

Transport of Rhodamine 123

Efflux of rhodamine 123 was analyzed in cells incubated in the presence of trypan blue and the MDR1 inhibitor GF120918. Cells not exposed to the inhibitor served as controls. The results of this analysis indicated that GF120918 slowed the efflux of rhodamine 123 from the cells. A rate constant of efflux was calculated and it was found that in the presence of GF120918, rate constant of efflux was about 10% of the control rate constant.

In addition to efflux, the effect of GF120918 on the uptake of rhodamine 123 was determined at a single time point. The GF120918-treated cells exhibited a greater initial fluorescence due to the inhibition of rhodamine 123 efflux by GF120918.

Example 2

Effect of MDR1 Inhibitors on Efflux and Intracellular Fluorescence

MRP inhibitors, verapamil, cyclosporin A and amprenavir were analyzed for inhibiting the efflux of rhodamine 123 with trypan blue to quench extracellular fluorescence. The results of this analysis indicated that 100 µM verapamil reduced rhodamine 123 efflux by about 95%, whereas 2 µg/mL cyclosporin A reduced rhodamine 123 efflux by about 80% and 100 µM amprenavir reduced rhodamine 123 efflux by about 75%. These results were consistent with the values obtained for initial fluorescence in the cells treated with these inhibitors.

Example 3

Intracellular Content of Fluorescent Drug Efflux Probes in Various Cell Types

Figure 1B:
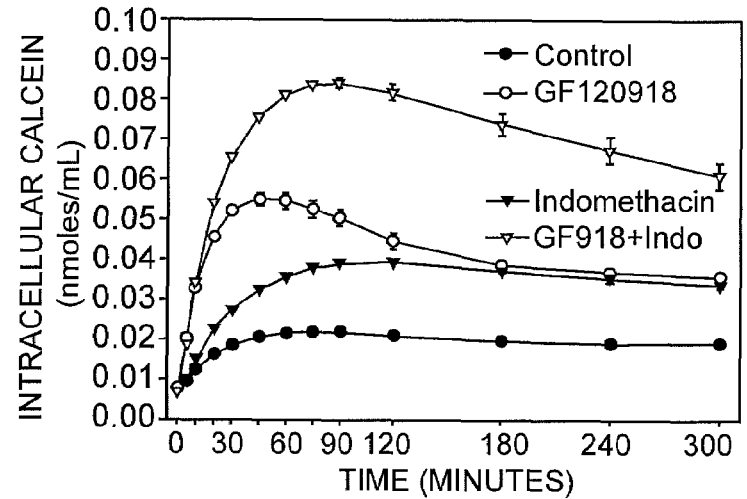
Figure 1C:
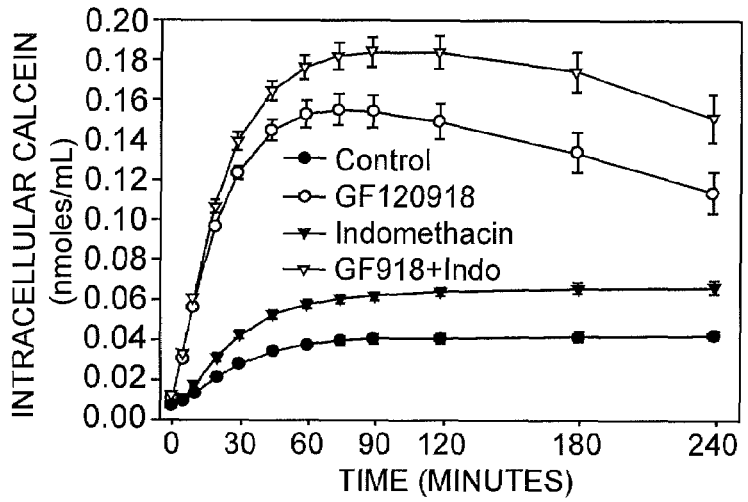
Figure 2A:
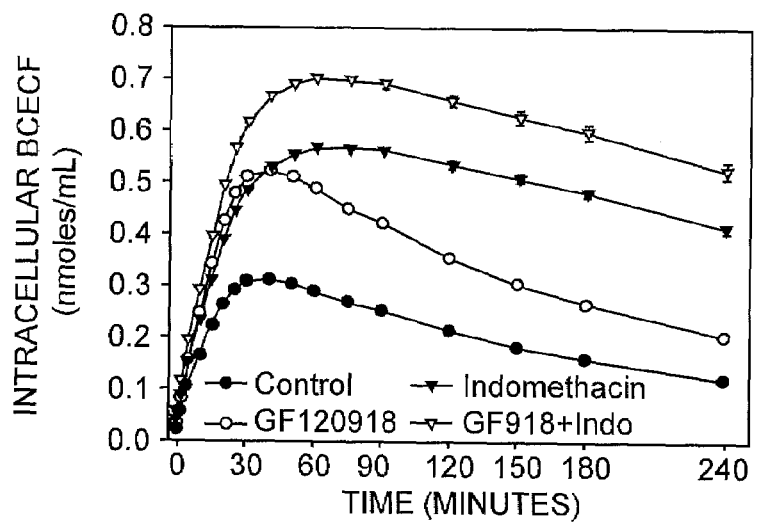
FIGS. 2A-2C show intracellular accumulation of BCECF-AM (1 µM) in MDCK-MDR1 (FIG. 2A), Caco2 (FIG. 2B), and BBMEC (FIG. 2C) cells exposed to MDR1 inhibitor GF120918, MRP inhibitor indomethacin, or GF120918 in combination with indomethacin. Trypan blue (0.04%) was used to quench extracellular fluorescence.
Figure 2B:
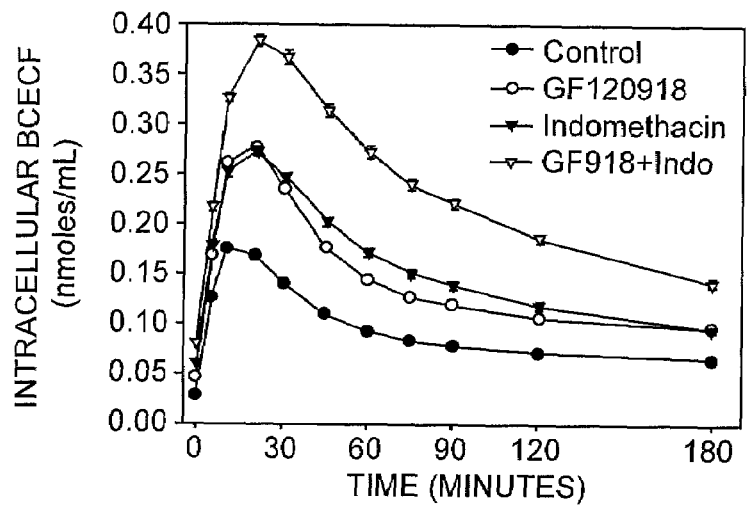
Figure 2C:
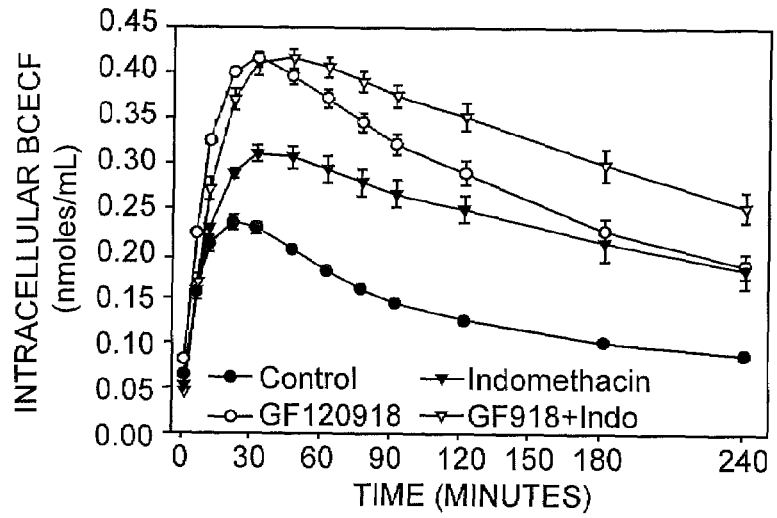
Figure 3A:
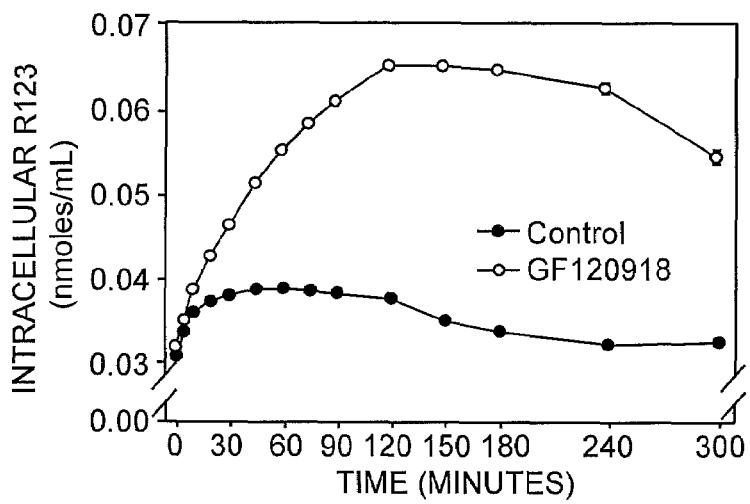
FIGS. 3A-3C show intracellular accumulation of rhodamine 123 (3.2 µM) in MDCK-MDR1 (FIG. 3A), Caco2 (FIG. 3B), and BBMEC (FIG. 3C) cells exposed to MDR1 inhibitor GF120918, MRP inhibitor indomethacin, or GF120918 in combination with indomethacin. Trypan blue (0.1%) was used to quench extracellular fluorescence.
Figure 3B:
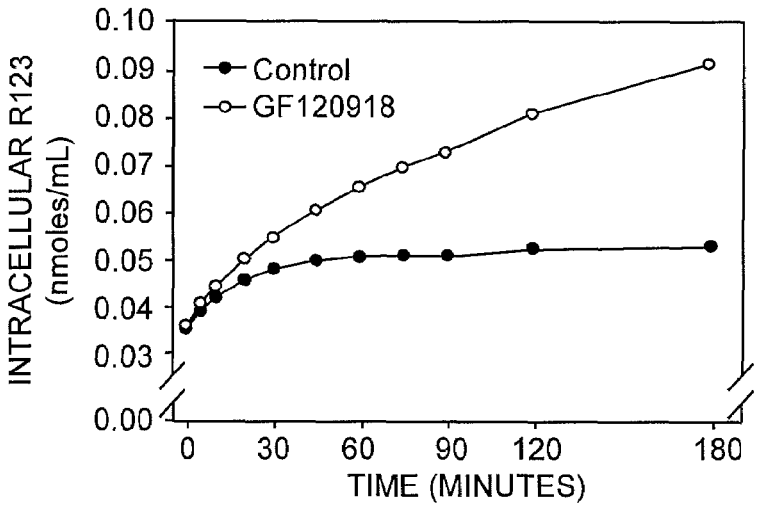
Figure 3C:
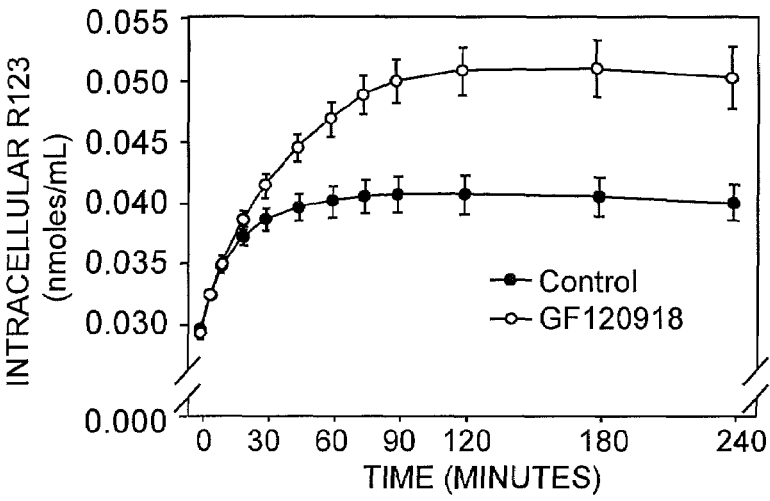

Using the assay of the present invention, the intracellular accumulation of calcein-AM (1 µM; FIGS. 1A-C), BCECF-AM (1 µM; FIGS. 2A-C) and rhodamine 123 (3.2 µM; FIGS. 3A-C) in the presence of 0.04% or 0.1% trypan blue was monitored in MDCK-MDR1 (FIG. 1A, FIG. 2A, FIG. 3A), Caco2 (FIG. 1B, FIG. 2B, FIG. 3B), and BBMEC (FIG. 1C, FIG. 2C, FIG. 3C) cells exposed to MDR1 inhibitor GF120918, MRP inhibitor indomethacin, or GF120918 in combination with indomethacin. The results of this analysis indicated that GF120918 and indomethacin inhibited the activity of the respective MDR proteins resulting in an increase in the intracellular accumulation of calcein-AM, BCECF, and rhodamine 123 in the cell types tested.

Example 4

Intracellular Accumulation of Calcein in the Presence of Therapeutic Agents

To determine whether known therapeutic agents modulate the intracellular accumulation of calcein-AM, MDCK-MDR1 cells were incubated in the presence of trypan blue and three concentrations of 5-fluorouracil, amprenavir and risperidone. Intracellular accumulation was monitored for 300 minutes in a 96-well format and the area under curve for each treatment was determined. This data is presented in Table 1. The larger the area under the curve, the greater the intracellular accumulation of calcein and, by extension, the greater the influence of the therapeutic agent on MDR protein activity.

TABLE 1

| Drug | Concentration (µM) | Area Under the Curve ± SEM | Ratio to Control |
|---|---|---|---|
| Control | 0 | 2.56 ± 0.106 | 1 |
| GF120918 | 3.2 | 22.57 ± 0.729* | 8.81 |
| 5-Fluorouracil | 1 | 3.07 ± 0.217 | 1.20 |
| | 10 | 3.33 ± 0.269 | 1.30 |
| | 100 | 2.24 ± 0.322 | 0.87 |
| Amprenavir | 1 | 4.06 ± 0.518 | 1.58 |
| | 10 | 5.44 ± 0.357* | 2.12 |
| | 100 | 16.25 ± 0.798* | 6.34 |

TABLE 1-continued

| Drug | Concentration (µM) | Area Under the Curve ± SEM | Ratio to Control |
|---|---|---|---|
| Risperidone | 1 | 3.92 ± 0.412 | 1.53 |
| | 10 | 5.62 ± 0.259 | 2.19 |
| | 100 | 17.02 ± 0.310* | 6.64 |

*$p < 0.01$ as determined by ANOVA and Dunnett's post-hoc comparisons. Controls included no agents. GF120918 was used a positive control and 5-fluorouracil was used as a negative control as it has been shown to not interact with MDR proteins.

The results of this analysis showed that amprenavir and risperidone increased the area under the curve of calcein significantly above the control, indicating a strong interaction with MDR proteins.

What is claimed is:

1. A high-throughput method for real-time monitoring of multi-drug resistance protein activity comprising
   a) contacting a cell expressing a multi-drug resistance protein with a fluorescent drug efflux probe, said fluorescent drug efflux probe being a rhodamine, and an o-tolidine-based dye for quenching the extracellular fluorescence of the probe, said o-tolidine-based dye being selected from the group consisting of Trypan Blue and Evans Blue; and
   b) determining the intracellular accumulation of the fluorescent drug efflux probe in the cell thereby monitoring multi-drug resistance protein activity of the cell.

2. A real-time, high-throughput method for identifying a modulator of a multi-drug resistance protein comprising
   a) contacting a cell expressing a multi-drug resistance protein with a test agent, a fluorescent drug efflux probe, said fluorescent drug efflux probe being a rhodamine, and an o-tolidine-based dye for quenching the extracellular fluorescence of the probe, said o-tolidine-based dye being selected from the group consisting of Trypan Blue and Evans Blue; and
   b) determining the intracellular accumulation of the fluorescent drug efflux probe in the cell, wherein an increase in the intracellular accumulation of the fluorescent drug efflux probe is indicative of a multi-drug resistance protein inhibitor and a decrease in the intracellular accumulation of the fluorescent drug efflux probe is indicative of a multi-drug resistance protein activator.

3. A real-time, high-throughput method for assessing multi-drug resistance in a cell, said method comprising
   a) contacting a cell suspected of overexpressing a multi-drug resistance protein with a fluorescent drug efflux probe, said fluorescent drug efflux probe being a rhodamine, and an o-tolidine-based dye for quenching the extracellular fluorescence of the probe, said o-tolidine-based dye being selected from the group consisting of Trypan Blue and Evans Blue; and
   b) determining the intracellular accumulation of the fluorescent drug efflux probe in the cell, wherein a decrease in the accumulation of the fluorescent drug efflux probe in the cell as compared to a control or standard is indicative that said cell is a multi-drug resistant cell.

4. A kit for real-time, high-throughput monitoring of multi-drug resistant protein activity comprising a fluorescent drug efflux probe, said fluorescent drug efflux probe being a rhodamine, and an o-tolidine-based dye for quenching the extracellular fluorescence of the probe, said o-tolidine-based dye being selected from the group consisting of Trepan Blue and Evans Blue and instructions for the use of said probe and said dye in carrying out said monitoring.

* * * * *